United States Patent
Zoeller

(10) Patent No.: US 11,337,995 B2
(45) Date of Patent: May 24, 2022

(54) PERIPHERAL NEUROPATHY COMPOSITION AND RELATED METHODS

(71) Applicant: Epsom-It, Inc., Edina, MN (US)

(72) Inventor: Matthew Zoeller, Chicago, IL (US)

(73) Assignee: Epsom-It, Inc., Edina, MN (US)

( * ) Notice: Subject to any disclaimer, the term of this patent is extended or adjusted under 35 U.S.C. 154(b) by 0 days.

(21) Appl. No.: 16/675,568

(22) Filed: Nov. 6, 2019

(65) Prior Publication Data

US 2020/0138856 A1    May 7, 2020

Related U.S. Application Data

(63) Continuation of application No. 62/756,172, filed on Nov. 6, 2018.

(51) Int. Cl.

| | | |
|---|---|---|
| *A61K 33/04* | (2006.01) | |
| *A61K 31/714* | (2006.01) | |
| *A61K 47/02* | (2006.01) | |
| *A61K 47/24* | (2006.01) | |
| *A61K 47/34* | (2017.01) | |
| *A61K 9/00* | (2006.01) | |
| *A61K 9/107* | (2006.01) | |

(52) U.S. Cl.
CPC ............ *A61K 33/04* (2013.01); *A61K 9/0014* (2013.01); *A61K 9/107* (2013.01); *A61K 31/714* (2013.01); *A61K 47/02* (2013.01); *A61K 47/24* (2013.01); *A61K 47/34* (2013.01)

(58) Field of Classification Search
CPC ...... A61K 33/04; A61K 9/0014; A61K 9/107; A61K 47/02; A61K 47/34; A61K 31/714; A61K 47/24
USPC ........................................................ 514/52
See application file for complete search history.

(56) References Cited

U.S. PATENT DOCUMENTS

| | | |
|---|---|---|
| 3,880,996 A | 4/1975 | Fisher |
| 4,456,627 A | 6/1984 | Van Heteren et al. |
| 4,595,586 A | 6/1986 | Flom |
| 5,035,890 A | 7/1991 | Braun |
| 5,216,033 A | 6/1993 | Pereira et al. |
| 5,246,918 A | 9/1993 | Behan |
| 5,371,089 A | 12/1994 | Rattan |
| 5,536,499 A | 7/1996 | Znaiden et al. |
| 5,795,573 A | 8/1998 | Paradise |
| 5,898,037 A | 4/1999 | Marx |
| 5,910,512 A | 6/1999 | Conant |
| 5,922,764 A | 7/1999 | Cantin et al. |
| 5,989,037 A | 11/1999 | Ruque |
| 6,150,403 A | 11/2000 | Biedermann et al. |
| 6,331,306 B1 | 12/2001 | Afriat et al. |
| 6,344,188 B1 | 2/2002 | Silva et al. |
| 7,871,647 B1 | 1/2011 | Paradise |
| 9,364,402 B1 | 6/2016 | Garcia et al. |
| 10,117,894 B2 | 11/2018 | Zollinger et al. |
| 2001/0011083 A1* | 8/2001 | Barr ..................... A61K 36/752 514/159 |
| 2003/0157185 A1 | 8/2003 | Paradise |
| 2004/0030056 A1 | 2/2004 | Bloom |
| 2006/0292245 A1 | 12/2006 | Schmit |
| 2007/0207107 A1* | 9/2007 | Winckle ............... A61K 9/0014 424/70.12 |
| 2008/0317873 A1* | 12/2008 | Schmit ................. A61K 9/0014 424/709 |
| 2010/0173007 A1 | 7/2010 | Dileva |
| 2016/0101139 A1 | 4/2016 | Paradise |
| 2016/0101141 A1 | 4/2016 | Paradise |
| 2016/0106797 A1 | 4/2016 | Paradise |
| 2016/0106798 A1 | 4/2016 | Paradise |

OTHER PUBLICATIONS

Dow Corning 3225C (published before 2004), http://www.infochems.co.kr/chemdb/product_content.asp?product_id=45363 (Year: 2004).*
OCT Product News dated Apr. 2004 (1 page). Printed on Feb. 18, 2011.

* cited by examiner

*Primary Examiner* — Yih-Horng Shiao
(74) *Attorney, Agent, or Firm* — DeWitt LLP

(57) ABSTRACT

A analgesic composition for topical application is provided that includes magnesium sulfate and a source of vitamin B12 in an amount effective for providing pain relief associated with peripheral neuropathy. The composition has a viscosity effective for allowing topical application of the composition to an afflicted area where the magnesium sulfate and vitamin B12 is absorbed through the dermis to the subcutaneous to provide pain relief relating to symptoms of peripheral neuropathy. The composition provides the novel benefits of being portable, easily dispensed, and provides a higher concentration of applied magnesium sulfate and vitamin B12 than the traditional dispensing method of Epsom Salt soaking solutions.

17 Claims, No Drawings

PERIPHERAL NEUROPATHY COMPOSITION AND RELATED METHODS

RELATED APPLICATION

The present application claims the benefit of U.S. Provisional Application No. 62/756,172 filed Nov. 6, 2018, which is hereby incorporated herein in its entirety by reference.

TECHNICAL FIELD

The present invention is directed to a topical pain relief composition that can be applied to the epidermis and be absorbed through the dermis to provide pain relief of subcutaneous joints and muscle discomfort and neuralgia, as well as, peripheral neuropathy. More particularly, an analgesic composition capable of topical application is provided that includes magnesium sulfate in an amount effective for providing relief. The present invention is also directed to a method of delivery of a topical pain relief composition so that the analgesic composition can be applied to the epidermis and be absorbed through the dermis to the subcutaneous to provide pain relief relating to symptoms of peripheral neuropathy.

BACKGROUND

People have long enjoyed the ameliorating effects of magnesium sulfate on their aching joints and muscles in the form of an Epsom salt bath and soaking the afflicted area. This is inconvenient in that the magnesium sulfate must be thoroughly dissolved, usually in warm water, and the individual is limited to a stationary position while soaking the afflicted area in the bath. Moreover, treatments using Epsom salts are not very portable and tend to be limited to use in the home. Epsom salt baths have also been used to treat neuropathy in feet.

Neuropathy refers to the many conditions that involve damage to the peripheral nervous system, the vast communication network that sends signals between the central nervous system (the brain and spinal cord) and all other parts of the body. The peripheral nervous system controls body movements, sensations, and automatic functions like blood pressure and sweating. If your nerves are disrupted or damaged, a variety of symptoms may appear depending on the type of nerves that are disrupted or damaged. It has been estimated that neuropathy in feet affects 2.4% of the population, 8% of people over age 55 experience the pain associated with neuropathy, and more than 22 million people in the United States have been estimated to have some form or peripheral neuropathy. While more than 100 types of peripheral neuropathy have been identified, diabetes is a leading cause of neuropathy, but neuropathy can be inherited or caused by a number of conditions, infections, other diseases, and trauma, each with its own symptoms and prognosis, including, but not limited to alcoholism, autoimmune disease, diabetes, exposure to poisons, medications, infections, inherited disorders, trauma or pressure on the nerve, tumors, bone marrow disorders, and other kidney, liver, connective tissue and thyroid diseases and conditions.

Symptoms from neuropathy can range from mild to disabling with symptoms depending on the type of nerve fibers affected and the type and severity of damage. Symptoms may develop over days, weeks, or years. Symptoms may include weakness, numbness and pain, usually in the hands and feet, but can also affect other areas of the body, and usually gets worse over time. People with peripheral neuropathy generally describe the associated pain as stabbing, burning or tingling.

Treatment goals for aching joints and muscles and neuropathy are to manage the condition causing the neuropathy and to relieve symptoms. Besides medications used to treat conditions associated with the aching joint, muscle, or neuropathy, medications are often used to relieve the associated symptoms, including over-the-counter pain medications such as nonsteroidal anti-inflammatory drugs or prescribed painkillers, medications containing opioids or oxycodone, topical treatments containing capsaicin and antidepressants. Such medications, however, may have undesired side effects, cause skin burning or irritation and/or lead to dependence and addiction. Besides some medications containing capsaicin that can cause an unpleasant burning sensation, some medications may also contain paraffin that are now believed to be carcinogenic. Treatment may also include various therapies and procedures to help ease the symptoms.

Accordingly, there is a need in the industry for pain relief associated with joint, muscle and/or neuropathy that is cost-effective and efficient, portable and convenient for the consumer to use, eliminates unnecessary side effects and dependency issues, does not contain undesirable components that cause burning or are carcinogenic, does not require the user to undergo therapies or procedures, or to remain stationary during treatment.

SUMMARY OF THE INVENTION

An analgesic composition is provided that has a viscosity effective for allowing its topical application on an area in need of pain relief relating to peripheral neuropathy, the analgesic composition having an aqueous phase that includes magnesium sulfate, at least one water-soluble carrier, at least one preservative, a source of vitamin B12, and water, and also a silicon phase that includes at least one water-insoluble carrier, a primary emulsifier, and a skin conditioning agent, wherein the aqueous phase and a silicone phase are provided as a water-in-silicone inverse phase emulsion. The analgesic composition may be a lotion, foam, paste, body rub, cream, gel, serum, stick-type solid, or sprayable solution which when applied leaves a film of the magnesium sulfate and vitamin B12 on the user's skin that are readily absorbed through providing pain relief associated with peripheral neuropathy.

In one aspect of the present invention, the analgesic composition is provided having magnesium sulfate in an amount of about 15 to about 30 weight percent, the source of vitamin B12 in an amount of about 0.001 to about 1 weight percent, the at least one water-soluble carrier in an amount of about 0.5 to about 6 weight percent of the total weight, a humectant in an amount of about 1 to about 10 weight percent, the at least one preservative in an amount of about 0.5 to about 6.0 weight percent, and water in an amount of about 35 to about 65 weight percent, within the aqueous phase; and cyclomethicone in an amount of about 5 to about 25 weight percent, dimethicone, dimethiconol, or a mixture in an amount of about 0.7 to about 1.0 weight percent, a primary emulsifer in an amount of about 0.5 to about 3.0 weight percent, and C12-15 alkyl benzoate in an amount of about 0.5 to about 5.0 weight percent, within silicone phase, of the water-in-silicone inverse phase emersion.

In one aspect of the present invention, the analgesic composition is provided having about 15 to about 30 weight percent magnesium sulfate (preferably about 20 to about 25 weight percent), about 0.001 to about 1 weight percent vitamin B12 (preferably about 0.05 to about 0.20 weight percent, more preferably the vitamin B12 is cyanocobalamin), about 0.5 to about 6 weight percent water-miscible solvent (preferably about 1.0 to about 3.0 weight percent butylene glycol and/or about 1.0 to about 2.0 weight percent ethoxydiglycol), about 0.5 to about 10 weight percent humectant (preferably about 0.5 to about 3.0 weight percent glycerin), about 0.5 to about 6.0 weight percent preservative (preferably about 0.5 to about 1.0 weight percent of diazolidinyl urea, iodopropynyl butylcarbamate, phenoxyethanol, ethylhexyl glycernin, caprylyl glycol, or mixtures thereof), about 6 to about 35 weight percent water-insoluble carrier (preferably about 22.0 to about 25.0 weight percent cyclomethicone and about 0.7 to about 1.0 weight percent dimethicone and/or dimethiconol), about 0.5 to about 3.0 weight percent emulsifier (preferably about 0.8 to about 1.1 weight percent of PPG/PEG 18/18 dimethicone), about 0.5 to about 5.0 weight percent texture enhancer (preferably about 0.5 to about 2.0 weight percent C12-15 alkyl benzoate), and water in a quantity sufficient to bring the composition to 100 weight percent (preferably about 35 to about 65 weight percent, more preferably about 45 to about 55 weight percent water). Preferably, the composition has a viscosity of at least about 10,000 cps to about 25,000 cps at 25° C. (Brookfield), and a viscosity of no more than about 25,000 cps at 25° C.

In another aspect of the present invention, the analgesic composition for alleviating neuropathy is provided as a water-in-silicone inverse-phase emulsion in the form of a lotion, the composition including an aqueous phase having about 15 to about 30 weight percent magnesium sulfate (preferably about 20 to about 25 weight percent), about 0.001 to about 1 weight percent vitamin B12 (preferably about 0.05 to about 0.20 weight percent, more preferably the vitamin B12 is cyanocobalamin), about 0.5 to about 6 weight percent water-miscible solvent (preferably about 1.0 to about 3.0 weight percent butylene glycol and/or about 1.0 to about 2.0 weight percent ethoxydiglycol), about 0.5 to about 10 weight percent humectant (preferably about 0.5 to about 3.0 weight percent glycerin), about 0.5 to about 6.0 weight percent preservative (preferably about 0.5 to about 1.0 weight percent of diazolidinyl urea, iodopropynyl butylcarbamate, phenoxyethanol, ethylhexyl glycernin, caprylyl glycol, or mixtures thereof), and water in a quantity sufficient to bring the composition to 100 weight percent (preferably about 35 to about 65 weight percent, more preferably about 45 to about 55 weight percent water), and a silicone phase having about 6 to about 35 weight percent water-insoluble carrier (preferably about 22.0 to about 25.0 weight percent cyclomethicone and about 0.5 to about 2.0 weight percent dimethicone and/or dimethiconol), about 0.5 to about 3.0 weight percent emulsifier (preferably about 0.75 to about 1.5 weight percent of PPG/PEG 18/18 dimethicone), about 0.5 to about 5.0 weight percent texture enhancer (preferably about 0.5 to about 2.0 weight percent C12-15 alkyl benzoate). Preferably, the composition has a viscosity of at least about 10,000 cps to about 25,000 cps at 25° C. (Brookfield), and a viscosity of no more than about 25,000 cps at 25° C.

In certain aspects, the analgesic composition is produced by mixing the silicon phase constituents in a vessel to form the silicone phase. In a separate vessel, the aqueous phase constituents are mixed to the aqueous phase. The aqueous phase is then mixed into the silicone phase over a period of time to provide the water-in-silicone inverse-phase emulsion.

In one certain aspect of the present invention, the analgesic composition is prepared by dissolving about 15 to about 25 weight percent of magnesium sulfate in about 45 to about 55 weight percent water in a vessel heated to a temperature of about 40 to about 45° C. Upon the magnesium sulfate dissolving into solution, the remaining aqueous constituents were then added and mixed to the solution that included glycerin in an amount of about 0.5 to about 3.0 weight percent glycerin, about 1.0 to about 2.0 weight percent ethoxydiglycol, about 0.5 to about 1.0 weight percent of diazolidinyl urea and iodopropynyl butylcarbamate dissolved in a base of 60% propylene glycol, and about 0.05 to about 0.20 weight percent vitamin B12 (cyanocobalamin), to form an aqueous phase solution. The silicone phase solution was prepared by mixing the silicone constituents in a separate vessel, which included about 22.0 to about 25.0 weight percent cyclomethicone, about 0.5 to about 2.0 weight percent dimethicone and/or dimethiconol, about 0.75 to about 1.5 weight percent of PPG/PEG 18/18 dimethicone), and about 0.5 to about 2.0 weight percent C12-15 alkyl benzoate. The aqueous phase solution was then slowly added to the silicone phase solution with gentle mixing at about 120 to about 600 rpm over a period of time of at least about 30 minutes, preferably about 60 to about 120 minutes, until all the constituents were fully combined to form a water-in-silicone inverse-phase emulsion. Once the aqueous phase was completely mixed into the silicone phase, the mixture was then homogenized using high shear at about 1200 to about 3500 rpm in an in-process homogenizer for a period of time of about 20 to about 30 minutes while recirculating the batch to effect a stable, smooth water-in-silicone inverse-phase emulsion product. Preferably, the analgesic composition has a viscosity of at least about 10,000 cps to about 25,000 cps at 25° C. (Brookfield), and a viscosity of no more than about 25,000 cps at 25° C.

In one aspect of the present invention, the analgesic composition is free of parabens, which includes at least methylparaben, ethylparaben, propylparaben, or butylparaben. In some other aspects of the present invention, the analgesic composition is free of capsaicin or capsicum. In some other aspects of the present invention, the analgesic composition is substantially free of any oils.

In one aspect of the present invention, the analgesic composition is applied to the epidermis of a human to alleviate pain in joints and/or muscles associated with peripheral neuropathy.

The above summary is not intended to describe each illustrated embodiment or every implementation of the subject matter hereof. The figures and the detailed description that follow more particularly exemplify various embodiments.

DETAILED DESCRIPTION

The present invention provides a pain relief composition comprising a water-in-silicone inverse-phase emulsion, the water-in-silicone inverse-phase emulsion comprising an aqueous phase comprising aqueous constituents, including magnesium sulfate, blended together to form the aqueous phase of the water-in-silicone inverse-phase emulsion, and a silicone phase comprising a miscible solution of silicone and lipid constituents blended together to form the silicone phase, wherein the aqueous phase having been added to the silicone phase to form the water-in-silicone inverse-phase emulsion.

The pain relief composition of the invention may be prepared in a variety of topical application or administration formulations, including lotion, gel, cream, paste, foam, body rub, serum, stick-type solid, sprayable solution, or the like for convenient application by the user. The pain relief composition of the invention is readily absorbed by the skin to provide relief from muscle aches, arthritis pain, joint stiffness and peripheral neuropathy. The composition of the present invention provides a greater concentration of Epsom salt activity in a topical delivery form than previously provided in traditional dissolved Epsom salt soaking preparations. In some aspects, the analgesic composition provides a level of delivery of magnesium sulfate that exceeds a standard Epsom Salt bath by a factor of at least 10.

All weight percents for ingredients described herein are based on the total weight of the composition unless specified otherwise.

The analgesic composition of the present invention generally comprises magnesium sulfate provided in an aqueous phase of the water-in-silicone inverse-phase emulsion. The magnesium sulfate provides ameliorating pain relief to aching joints and muscles. The magnesium sulfate is an inorganic salt with the formula $MgSO_4(H_2O)_x$, where x is greater than or equal to 0 and less than or equal to 7. The magnesium sulfate can be obtained from commercially available Epsom salts. In certain aspects of the present invention, the magnesium sulfate is USP grade magnesium sulfate heptahydrate. The compositions of the present invention may include magnesium sulfate in an amount of at least 15% up to about 30% by weight of the total weight of the composition, in some aspects between about 18% and about 28% by weight of the total weight of the composition, and in some other aspects between about 20% and about 25% by weight of the total weight of the composition. In some aspects, the compositions of the present invention include at least 15% by weight of magnesium sulfate and up to about 30% by weight, in some aspects up to about 28% by weight, and in some other aspects up to about 25% by weight of the total weight of the composition.

The analgesic composition of the present invention may also contain vitamin B12 in the aqueous phase of the water-in-silicone inverse-phase emulsion. Without wishing to be bound by theory, the vitamin B12 in the composition is believed to aid or boost the effect of the magnesium sulfate by providing pain relief to aching joints and muscles. The compositions of the present invention may include vitamin B12 from cyanocobalamin, methylcobalamin, or a mixture thereof in an amount of at least 0.01% up to about 1% by weight of the total weight of the composition, in some aspects between about 0.05% and about 0.5% by weight of the total weight of the composition, and in some other aspects between about 0.07% and about 0.25% by weight of the total weight of the composition. In some aspects, the compositions of the present invention include at least 0.01% by weight of cyanocobalamin (vitamin B12 in mannitol) and up to about 1% by weight, in some aspects up to about 0.5% by weight, in some aspects up to about 0.4% by weight, in some aspects up to about 0.3% by weight, in some aspects up to about 0.2% by weight, and in some other aspects up to about 0.15% by weight of the total weight of the composition.

The analgesic composition of the present invention may also contain one or more water-miscible solvents in the aqueous phase of the water-in-silicone inverse-phase emulsion. Preferred water-miscible solvents are preferably dermatologically acceptable. In some aspects, the water-miscible solvent is ethoxydiglycol (also known as diethylene glycol monethyl ether), butylene glycol, glycerin, and mixtures thereof. In some aspects, the water-miscible solvent is chosen from ethoxydiglycol, butylene glycol, glycerin, propylene glycol, dipropylene glycol, and mixtures thereof.

In some aspects, the analgesic composition of the present invention contains ethoxydiglycol as a water-miscible solvent in the aqueous phase to induce cutaneous permeation of water-soluble actives, such as magnesium sulfate, cyanocobalamin (vitamin B12), and the like, into the dermal and hair keratin. The compositions of the present invention may include ethoxydiglycol in an amount of at least 0.05% up to about 5% by weight of the total weight of the composition, in some aspects between about 0.1% and about 3% by weight of the total weight of the composition, and in some other aspects between about 0.5% and about 2% by weight of the total weight of the composition. In some aspects, the compositions of the present invention include at least 0.5% by weight of ethoxydiglycol and up to about 5% by weight, in some aspects up to about 4% by weight, in some aspects up to about 3% by weight, and in some other aspects up to about 2% by weight of the total weight of the composition.

In some aspects, the analgesic composition of the present invention contains butylene glycol as a water-miscible solvent in the aqueous phase to decrease the tackiness of cyanocobalamin (vitamin B12) and/or increase the stability of the water composition phase of the water-in-silicone inverse-phase emulsion. The compositions of the present invention may include butylene glycol in an amount of at least 0.5% up to about 10% by weight of the total weight of the composition, in some aspects between about 0.75% and about 5% by weight of the total weight of the composition, and in some other aspects between about 1% and about 3% by weight of the total weight of the composition. In some aspects, the compositions of the present invention include at least 0.5% by weight of butylene glycol and up to about 10% by weight, in some aspects up to about 5% by weight, in some aspects up to about 3% by weight, and in some other aspects up to about 2% by weight of the total weight of the composition.

In some aspects, the analgesic composition of the present invention contains glycerin as a humectant and/or internal phase stabilizer in the aqueous phase. The compositions of the present invention may include glycerin in an amount of at least 0.5% up to about 10% by weight of the total weight of the composition, in some aspects between about 0.75% and about 5% by weight of the total weight of the composition, and in some other aspects between about 1% and about 3% by weight of the total weight of the composition. In some aspects, the compositions of the present invention include at least 0.5% by weight of glycerin and up to about 10% by weight, in some aspects up to about 5% by weight, in some aspects up to about 3% by weight, and in some other aspects up to about 2% by weight of the total weight of the composition.

The analgesic composition of the present invention may also contain one or more preservatives in the aqueous phase of the water-in-silicone inverse-phase emulsion, the one or more preservatives employed to grant shelf-life stability and/or prevent microbial contamination. In some aspects, the preservative is diazolidinyl urea, iodopropynyl butylcarbamate, phenoxyethanol, ethylhexyl glycerin, caprylyl glycol, DMDM hydantoin, sodium benzoate, sodium dehydroacetate, potassium sorbate, or mixtures thereof. In some aspects, the pain relief composition of the present invention contains one or more preservatives in an amount of at least 0.01% up to about 2% by weight of the total weight of the composition, in some aspects between about 0.05% and about 1.5% by weight of the total weight of the composition, and in some other aspects between about 0.1% and about 1% by weight of the total weight of the composition. In some aspects, the compositions of the present invention include at least 0.1% by weight of the one or more preservatives and up to about 2% by weight, in some aspects up to about 1.5% by weight and in some other aspects up to about 1% by weight of the total weight of the composition. In some aspects, the compositions of the present invention comprise diazolidinyl urea and iodopropynyl butylcarbamate in an amount of at least 0.01% up to about 2% by weight of the total weight of the composition, in some aspects between about 0.05% and about 1.5% by weight of the total weight of the composition, and in some other aspects between about 0.1% and about 1% by weight of the total weight of the composition. In some aspects, the compositions of the present invention comprise phenoxyethanol, ethylhexyl glycerine, or caprylyl glycol in an amount of at least 0.01% up to about 2% by weight of the total weight of the composition, in some aspects between about 0.05% and about 1.5% by weight of the total weight of the composition, and in some other aspects between about 0.1% and about 1% by weight of the total weight of the composition.

The analgesic composition of the present invention may comprise a water-insoluble carrier in the silicone phase comprising one or more silicone derivatives such as cyclomethicone, dimethicone or dimethiconol. The compositions of the present invention may include the one or more water-insoluble carriers in an amount of at least 5% up to about 35% by weight of the total weight of the composition, in some aspects between about 6% and about 30% by weight of the total weight of the composition, and in some other aspects between about 10% and about 27% by weight of the total weight of the composition. In some aspects, the compositions of the present invention include at least 5% by weight of the one or more water-insoluble carriers and up to about 35% by weight, in some aspects up to about 30% by weight, and in some other aspects up to about 27% by weight of the total weight of the composition.

In some aspects, the analgesic composition of the present invention contains cyclomethicone as a water-insoluble carrier in the silicone phase as a primary emulsifier and/or silicone emollients. The compositions of the present invention may include cyclomethicone in an amount of at least 5% up to about 35% by weight of the total weight of the composition, in some aspects between about 10% and about 30% by weight of the total weight of the composition, and in some other aspects between about 15% and about 25% by weight of the total weight of the composition. In some aspects, the compositions of the present invention include at least 5% by weight of cyclomethicone and up to about 35% by weight, in some aspects up to about 30% by weight, in some aspects up to about 28% by weight, and in some other aspects up to about 25% by weight of the total weight of the composition.

In some aspects, the analgesic composition of the present invention contains dimethicone and/or dimethiconol as a water-insoluble carrier in the silicone phase for aiding in emulsification and/or providing lubricity to the skin upon topical application. The compositions of the present invention may include dimethicone and/or dimethiconol in an amount of at least 0.5% up to about 10% by weight of the total weight of the composition, in some aspects between about 0.6% and about 5% by weight of the total weight of the composition, and in some other aspects between about 0.7% and about 1% by weight of the total weight of the composition. In some aspects, the compositions of the present invention include at least 0.5% by weight of dimethicone and up to about 10% by weight, in some aspects up to about 5% by weight, in some aspects up to about 2% by weight, and in some other aspects up to about 1% by weight of the total weight of the composition.

The analgesic composition of the present invention may comprise one or more primary emulsifiers in the silicone phase of the water-in-silicone inverse phase emulsion. In some aspects, the primary emulsifier is a nonionic alkyl modified silane ether emulsifier that is the primary means of entropic stability for the composition. In some aspects, the primary emulsifer is one or more dimethicone copolyols such as Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, Cetyl PEG/PPG-10/1 Dimethicone, bis-PEG/PPG-14/14 Dimethicone, and mixtures thereof. In some preferred aspects, the primary emulsifer is PPG/PEG 18/18 dimethicone. The compositions of the present invention may include the one or more primary emulsifiers in an amount of at least 0.5% up to about 3% by weight of the total weight of the composition, in some aspects between about 0.6% and about 2% by weight of the total weight of the composition, and in some other aspects between about 0.7% and about 1.5% by weight of the total weight of the composition. In some aspects, the compositions of the present invention include at least 0.5% by weight of the one or more water-insoluble carriers and up to about 3% by weight, in some aspects up to about 2% by weight, in some aspects up to about 1.5% by weight, and in some other aspects up to about 1.1% by weight of the total weight of the composition.

The analgesic composition of the present invention may comprise a one or more texture enhancers in the silicone phase. In some aspects, the texture enhancer is C12-15 alkyl benzoate, which is ester miscible with cyclomethicone and used to incorporate alkyl or olefin organic compounds into the composition, such as capsaicin, tocopherol, botanical oils such as calendula oil, clove bud oil, clove leaf oil, peppermint oil, and the like. In some aspects, C12-15 alkyl benzoate can be used to incorporate one or more other lipid-soluble additives including botanical triglyceride oils, botanically derived esters, cosmetic esters, cannabidiols, retinoids and their esters, and lipids aiding permeation into the stratus corneum, such as dimethyl isosorbide and emu (*Dromaius novaehollandiae*) oil. The compositions of the present invention may include C12-15 alkyl benzoate in an amount of at least 0.5% up to about 5% by weight of the total weight of the composition, in some aspects between about 0.75% and about 3% by weight of the total weight of the composition, and in some other aspects between about 1% and about 2% by weight of the total weight of the composition. In some aspects, the compositions of the present invention include at least 0.5% by weight of the C12-15 alkyl benzoate and up to about 5% by weight, in some aspects up to about 3% by weight, in some aspects up to about 2% by weight, and in some other aspects up to about 1% by weight of the total weight of the composition.

Ancillary ingredients, such as fragrance, colorants, tocopherol acetate (Vitamin E), aloe vera, emollients, moisturizing agents, plant extracts and botanical oil anti-inflammatories, or the like may optionally be included in the composition of the present invention. Exemplary botanical oil anti-inflammatories include tea tree oil, allantoin, clove bud oil, cloy leaf oil, peppermint oil, calendula and capsaicin. Exemplary plant extracts include *Arnica Montana* extract. The compositions of the present invention may include *Arnica Montana* extract in an amount of at least 0.001% up to about 1.0% by weight of the total weight of the composition, in some aspects between about 0.01% and about 1.0% by weight of the total weight of the composition, and in some other aspects between about 0.1% and about 1.0% by weight of the total weight of the composition. The composition may include about 0.01% to about 1.0%, in some aspects about 0.1 to about 1% by weight of these other optional ingredients. These optional ingredients should be non-irritating to the skin.

In some aspects, the analgesic composition includes sodium bicarbonate, which can be added in the aqueous phase. The compositions of the present invention may include sodium bicarbonate in an amount of at least 0.5% up to about 10% by weight, and in some other aspects between about 1.0% and 5.0% by weight, of the total weight of the composition.

In certain aspects of the present invention, an analgesic composition is provided that includes about 15 to about 30 weight percent magnesium sulfate (preferably about 20 to about 25 weight percent), about 0.001 to about 1 weight percent vitamin B12 (preferably about 0.05 to about 0.20 weight percent, more preferably the vitamin B12 is cyanocobalamin), about 0.5 to about 6 weight percent water-miscible solvent (preferably about 1.0 to about 3.0 weight percent butylene glycol and/or about 1.0 to about 2.0 weight percent ethoxydiglycol), about 0.5 to about 10 weight percent humectant (preferably about 0.5 to about 3.0 weight percent glycerin), about 0.5 to about 6.0 weight percent preservative (preferably about 0.5 to about 1.0 weight percent of diazolidinyl urea, iodopropynyl butylcarbamate, phenoxyethanol, ethylhexyl glycernin, caprylyl glycol, or mixtures thereof), about 6 to about 35 weight percent water-insoluble carrier (preferably about 22.0 to about 25.0 weight percent cyclomethicone and about 0.7 to about 1.0 weight percent dimethicone and/or dimethiconol), about 0.5 to about 3.0 weight percent emulsifier (preferably about 0.8 to about 1.1 weight percent of PPG/PEG 18/18 dimethicone), about 0.5 to about 5.0 weight percent texture enhancer (preferably about 0.5 to about 2.0 weight percent C12-15 alkyl benzoate), and water in a quantity sufficient to bring the composition to 100 weight percent (preferably about 35 to about 65 weight percent, more preferably about 45 to about 55 weight percent water). The composition may further optionally include about 0.1 to about 1 weight percent of one or more ancillary ingredients (preferably about 0.1 to about 1.0 weight percent per ancillary ingredient). Preferably, the composition has a viscosity of at least about 10,000 cps to about 25,000 cps at 25° C. (Brookfield), and a viscosity of no more than about 25,000 cps at 25° C. In certain aspects, the analgesic composition is a water-in-silicone inverse-phase emulsion provided as a topical application or administration formulation in the form of a lotion, gel, cream, paste, foam, body rub, serum, stick-type solid, or sprayable solution.

In another aspect of the present invention, an analgesic composition for alleviating neuropathy is provided as a water-in-silicone inverse-phase emulsion in the form of a lotion, the composition including an aqueous phase having about 15 to about 30 weight percent magnesium sulfate (preferably about 20 to about 25 weight percent), about 0.001 to about 1 weight percent vitamin B12 (preferably about 0.05 to about 0.20 weight percent, more preferably the vitamin B12 is cyanocobalamin), about 0.5 to about 6 weight percent water-miscible solvent (preferably about 1.0 to about 3.0 weight percent butylene glycol and/or about 1.0 to about 2.0 weight percent ethoxydiglycol), about 0.5 to about 10 weight percent humectant (preferably about 0.5 to about 3.0 weight percent glycerin), about 0.5 to about 6.0 weight percent preservative (preferably about 0.5 to about 1.0 weight percent of diazolidinyl urea, iodopropynyl butylcarbamate, phenoxyethanol, ethylhexyl glycernin, caprylyl glycol, or mixtures thereof), and water in a quantity sufficient to bring the composition to 100 weight percent (preferably about 35 to about 65 weight percent, more preferably about 45 to about 55 weight percent water), and a silicone phase having about 6 to about 35 weight percent water-insoluble carrier (preferably about 22.0 to about 25.0 weight percent cyclomethicone and about 0.5 to about 2.0 weight percent dimethicone and/or dimethiconol), about 0.5 to about 3.0 weight percent emulsifier (preferably about 0.75 to about 1.5 weight percent of PPG/PEG 18/18 dimethicone), about 0.5 to about 5.0 weight percent texture enhancer (preferably about 0.5 to about 2.0 weight percent C12-15 alkyl benzoate). The composition may further optionally include about 0.1 to about 1 weight percent of one or more ancillary ingredients (preferably about 0.1 to about 1.0 weight percent per ancillary ingredient). Preferably, the composition has a viscosity of at least about 10,000 cps to about 25,000 cps at 25° C. (Brookfield), and a viscosity of no more than about 25,000 cps at 25° C.

In certain aspects, the compositions of the present invention may be paraben-free, such that the compositions have no parabens (such as methylparaben, ethylparaben, propylparaben, or butylparaben).

In certain aspects, the compositions of the present invention may be capsaicin-free and/or capsicum-free, such that the compositions have no capsaicin and/or capsicum, which may present a burning, tingling or irritating feeling to the user.

In certain aspects, the compositions of the present invention may be substantially free of any oils, including carrier oils, such as mineral oil, coconut oil, olive oil, baby oil, essential oils, grapeseed oil, hemp seed oil, evening primrose oil, and Vitamin E oils, or the like. In some aspects, the compositions of the present invention are free of sucrose, soy, casein, gluten, wheat, egg, milk, artificial colorings, artificial flavorings, yeast, gelatin, peanuts, fish, and/or tree nuts.

In certain aspects of the present invention, the composition is formulated for topical application on the skin, preferably applied as needed, to achieve the desired pain relief due to alleviate aching joints and/or muscles due to peripheral neuropathy. The composition of the present invention may be provided in a variety of formulations and viscosities, such as in a lotion, cream, foam, paste, gel, body rub, sprayable solution, serum, stick-type solid, or the like. Depending on the form of the composition, the composition may be rubbed, poured, or sprayed onto the skin. The composition is applied to the skin on an as needed basis for as long as the pain relieving effect is desired.

In another aspect of the invention, the composition has may be provided in a variety of formulations with the following viscosities: about 20 to about 4000 cps for sprayable liquids, serums, and the like; about 4000 to about 25,000 cps for lotions, liniments, and the like; about 20,000 to about 300,000 cps for creams, gels, pastes, ointments, and the like; and sedentary for stick solids.

It is further contemplated that the composition of the present invention may be provided in combination with a variety of other skin treatment compositions, such as medicated lotions, suntan lotions, moisturizers, anti-aging compositions, the like, or mixtures thereof.

Preparation of the Composition

In certain aspects of the present invention, the analgesic composition of the present invention is produced by blending the aqueous constituents together to form an aqueous phase. In some aspects, the aqueous phase has the magnesium sulfate completely dissolved. The silicone and lipid constituents are blended together to form a silicone phase. The aqueous phase is then slowly added to the silicone phase, such as 120 to about 600 rpm, with gentle mixing over at least about 30 minutes, preferably about 60 to about 120 minutes, until all the constituents are fully combined for form a water-in-silicone inverse-phase emulsion. The mixture is then homogenized using high shear at about 1200 to about 3500 rpm in an in-process homogenizer for a period of time of about 15 to about 40 minutes to effect a stable, smooth water-in-silicone inverse-phase emulsion product. In some aspects, the blending and mixing occurs at a temperature of about 40° C. or less.

In some aspects, the aqueous constituents comprising about 15 to about 30 weight percent magnesium sulfate (preferably about 20 to about 25 weight percent), about 0.001 to about 1 weight percent vitamin B12 (preferably about 0.05 to about 0.20 weight percent, more preferably the vitamin B12 is cyanocobalamin), about 0.5 to about 6 weight percent water-miscible solvent (preferably about 1.0 to about 3.0 weight percent butylene glycol and/or about 1.0 to about 2.0 weight percent ethoxydiglycol), about 0.5 to about 10 weight percent humectant (preferably about 0.5 to about 3.0 weight percent glycerin), about 0.5 to about 6.0 weight percent preservative (preferably about 0.5 to about 1.0 weight percent of diazolidinyl urea, iodopropynyl butylcarbamate, phenoxyethanol, ethylhexyl glycerine, caprylyl glycol, or mixtures thereof), and water in a quantity sufficient to bring the composition to 100 weight percent (preferably about 35 to about 65 weight percent, more preferably about 45 to about 55 weight percent water).

In some aspects, the silicone and lip constituents comprising the miscible solution of the silicone phase include about 6 to about 35 weight percent water-insoluble carrier (preferably about 22.0 to about 25.0 weight percent cyclomethicone and about 0.5 to about 2.0 weight percent dimethicone and/or dimethiconol), about 0.5 to about 3.0 weight percent emulsifier (preferably about 0.75 to about 1.5 weight percent of PPG/PEG 18/18 dimethicone), about 0.5 to about 5.0 weight percent texture enhancer (preferably about 0.5 to about 2.0 weight percent C12-15 alkyl benzoate).

In certain aspects, the analgesic composition comprising a water-in-silicone inverse-phase emulsion is provided as a topical application or administration formulation in the form of a lotion, gel, cream, paste, foam, body rub, serum, stick-type solid, or sprayable solution.

In certain aspects, the water-in-silicone inverse-phase emulsion has the physical appearance of a smooth lotion that can be topically applied to the skin with a silky texture to deliver the magnesium sulfate in the internal (disperse) phase in solution, not solid state. In some aspects, the lotion is hypoallergenic and nontoxic. The magnesium sulfate is preferably delivered at the level of about 20 to about 25 weight percent, which is near the saturation level for dissolution. The level of magnesium sulfate in the lotion exceeds that of a standard Epsom Salt bath by a factor of at least 10. Without wishing to be bound by theory, the vitamin B12 enhances and improves the relief from subcutaneous muscle and joint discomfort and neuralgia.

Example 1

An exemplary analgesic composition of the present invention can be formulated with the aqueous constituents in Table 1 blended together until the magnesium sulfate dissolves to form the aqueous phase, and the silicone and lipid constituents in Table 2 blended together to form the silicone phase. The aqueous phase can then slowly be added to the silicone phase with gentle mixing at about 120 to about 600 rpm over a period of time of at least about 30 minutes, preferably about 60 to about 120 minutes, until all the constituents were fully combined to form a water-in-silicone inverse-phase emulsion. The mixture can then be homogenized using high shear at about 1200 to about 3500 rpm in an in-process homogenizer for a period of time of about 15 to about 40 minutes to effect a stable, smooth water-in-silicone inverse-phase emulsion product. The blending of the aqueous constituents to form the aqueous phase, the silicone and lipid constituents to form the silicone phase, and the mixing of the aqueous phase into the silicone phase to form the water-in-silicone inverse-phase emulsion product all occur at a temperature of about 40° C. or less.

TABLE 1

| Aqueous Constituents of the Aqueous Phase. | |
|---|---|
| Aqueous Constituents | Weight Percent (% w/w) |
| Magnesium Sulfate Heptahydrate (USP grade) | 20.0-25.0 |
| Vitamin B12 (cyanocobalamin and/or methylcobalamin) | 0.10-0.20 |
| Butylene Glycol | 1.0-3.0 |
| Ethoxydiglycol | 1.0-2.0 |
| Glycerin | 1.0-3.0 |
| *Arnica Montana* Extract | 0.001-1.0 |
| Diazolidinyl Urea and Iodopropynyl Butylcarbamate or Phenoxyethanol, Ethylhexyl Glycerin, Caprylyl Glycol | 0.5-1.0 |
| Purified Water | q.s. to 100 (approximately 35-65) (preferably 45-55) |

TABLE 2

Silicone and Lipid Constituents of the Silicone Phase

| Silicone and Lipid Constituents | Weight Percent (% w/w) |
| --- | --- |
| Cyclomethicone (cyclodimethylpentasiloxane) | 22.0-25.0 |
| PPG/PEG 18/18 Dimethicone | 0.8-1.1 |
| Dimethicone and/or Dimethiconol | 0.7-1.0 |
| C12-15 Alkyl Benzoate | 1.0-2.0 |

Example 2

An exemplary analgesic composition of the present invention was formulated into a lotion with the aqueous constituents in Table 3 and the silicone constituents in Table 4. The aqueous constituents in Table 3 were blended together in a large jacketed vessel to form the aqueous phase. The magnesium sulfate was first dissolved in the allotted water by heating to a temperature of about 40 to about 45° C. and mixing until the magnesium sulfate completely dissolved in solution. The remaining aqueous constituents were then added in the order of Table 3 to the magnesium sulfate and water solution and uniformly mixed. The silicone constituents in Table 4 were mixed in a main jacketed mixing vessel at a temperature of about 40 to about 45° C. to form the silicone phase. The aqueous phase was then slowly be added to the silicone phase with gentle mixing at about 120 to about 600 rpm over a period of time of at least about 30 minutes, preferably about 60 to about 120 minutes, until all the constituents were fully combined to form a water-in-silicone inverse-phase emulsion. Once the aqueous phase was completely mixed into the silicone phase, the mixture was then homogenized using high shear at about 1200 to about 3500 rpm in an in-process homogenizer for a period of time of about 20 to about 30 minutes while recirculating the batch to effect a stable, smooth water-in-silicone inverse-phase emulsion product.

TABLE 3

Aqueous Constituents of the Aqueous Phase.

| Aqueous Constituents | Weight Percent (% w/w) | Mass (lbs.) |
| --- | --- | --- |
| Water deionized | 50.40 | 2016.00 |
| Magnesium Sulfate Heptahydrate (USP grade) | 20.00 | 800.00 |
| Glycerin USP | 1.00 | 40.00 |
| Ethoxydiglycol | 1.00 | 40.00 |
| Liquid Germall ® Plus (Diazolidinyl Urea and Iodopropynyl Butylcarbamate dissolved in a base of 60% propylene glycol) | 0.50 | 20.00 |
| Cyanocobalamin (vitamin B12 in mannitol) | 0.10 | 4.00 |

TABLE 4

Silicone and Lipid Constituents of the Silicone Phase

| Silicone and Lipid Constituents | Weight Percent (% w/w) | Mass (lbs.) |
| --- | --- | --- |
| Cyclomethicone D5 (cyclodimethylpentasiloxane) | 12.00 | 480.00 |
| Dimethiconol in Cyclomethicone (DC1401) | 5.00 | 200.00 |
| 12.5% dispersion of PPG/PEG 18/18 Dimethicone in Cyclomethicone (Dow Corning ® 5225C) | 9.00 | 360.00 |
| C12-15 Alkyl Benzoate | 1.00 | 40.00 |

The water-in-silicone inverse phase emulsion had a bright yellow-orange color with the appearance of a uniform viscous emulsion, a viscosity between 10,000 and 25,000 cps, and a specific gravity at 25° C. between 1.100 and 1.120, such that the composition was in the form of a lotion.

A female, 75 years of age, presenting peripheral neuropathic symptoms in the feet and ankles applied the lotion at bedtime to the feet and ankle area. Within a few minutes upon application, the female experienced a definite soothing effect ameliorating the effects of the peripheral neuropathy. The lotion applied prior to bedtime facilitated calming sensitized nerves in the toes, feet and ankles providing relief.

A male, 75 years of age, presenting peripheral neuropathic symptoms in the feet and ankles applied the lotion at bedtime to the feet and ankle area. The male experienced a calming of sensitized nerves in the toes, feet and ankles. The lotion provided a definite soothing effect ameliorating the effects of the peripheral neuropathy.

Numerous modifications and variations in practice of the invention are expected to occur to those skilled in the art upon consideration of the foregoing detailed description of the invention. Consequently, such modifications and variations are intended to be included within the scope of the following claims.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The invention claimed is:

1. An analgesic composition for topical application in relieving peripheral neuropathy, the analgesic composition comprising:
    an aqueous phase and a silicone phase provided as a water-in-silicone inverse phase emulsion;
    wherein the aqueous phase comprising magnesium sulfate in an amount from about 0.15 to about 30 weight percent based on the total weight of the composition, a water-soluble carrier consisting of ethoxydiglycol in an amount from 0.5 to about 5 weight percent based on the total weight of the composition, glycerine in an amount from 0.5 to about 10 weight percent based on the total weight of the composition and one of butylene glycol and propylene glycol, a third agent from at least one preservative in an amount from 0.5 to about 6.0 weight percent based on the total weight of the composition, optionally a source of vitamin B12, and water in an amount from about 35 to about 55 weight percent based on the total weight of the composition;
    wherein the silicone phase comprising at least one water-insoluble carrier comprising a cyclomethicone in an amount from about 5 to about 25 weight percent based on the total weight of the composition, a second agent from a primary emulsifier in an amount from 0.5 to about 3 weight percent based on the total weight of the composition, and a third agent from a skin conditioning agent; and
    wherein the analgesic composition has a viscosity from 20 to 10,000 cps to provide a liquid or serum form for topical application.

2. The analgesic composition of claim 1, wherein the magnesium sulfate comprises magnesium sulfate heptahydrate.

3. The analgesic composition of claim 1, wherein the magnesium sulfate is in an amount from about 20 to about 25 weight percent based on the total weight of the composition.

4. The analgesic composition of claim 1, wherein the primary emulsifier is a modified dimethicone, hydrophillically modified alkyl fatty acid esters of polyols, or mixtures thereof.

5. The analgesic composition of claim 1, wherein the cyclomethicone is cyclodimethylpentasiloxane.

6. The analgesic composition of claim 1, wherein the skin-conditioning agent comprises dimethicone.

7. The analgesic composition of claim 6, wherein dimethicone is present in an amount from about 0.70 to about 10.00 weight percent based on the total weight of the composition.

8. The analgesic composition of claim 1, wherein the primary emulsifer comprises a dimethicone copolyol.

9. The analgesic composition of claim 8, wherein the dimethicone copolyol is selected from the group consisting of Dimethicone polyethylene glycol (PEG)-8 Adipate, Dimethicone PEG-8 Benzoate, Dimethicone PEG-7 Phosphate, Dimethicone PEG-10 Phosphate, Dimethicone PEG/propylene glycol (PPG)-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, Cetyl PEG/PPG-10/1 Dimethicone, bis-PEG/PPG-14/14 Dimethicone, and mixtures thereof.

10. The analgesic composition of claim 8, wherein the dimethicone copolyol is present in an amount of about 0.80 to about 1.10 weight percent based on the total weight of the composition.

11. The analgesic composition of claim 1, wherein the analgesic composition has a viscosity of about 20 to about 4000 cps.

12. The analgesic composition of claim 1, wherein the analgesic composition is free of any coconut oil, olive oil, essential oils, grapeseed oil, hemp seed oil, or evening primrose oil.

13. The analgesic composition of claim 1, further comprising *Arnica montana* extract in an amount of at least 0.001% up to about 1.0% by weight of the total weight of the composition.

14. The analgesic composition of claim 1, further comprising sodium bicarbonate in an amount of at least 0.5% up to about 10% by weight of the total weight of the composition.

15. The analgesic composition of claim 1, wherein the analgesic composition has no parabens.

16. A method of manufacturing the analgesic composition of claim 1, the method comprising:
    blending two or more aqueous constituents in water to form an aqueous phase, wherein the two or more aqueous constituents include magnesium sulfate in an amount of about 20 to about 25 weight percent and the water-soluble carriers, and wherein the aqueous constituents are blended until the magnesium sulfate is dissolved in the aqueous phase;
    blending two or more water-insoluble constituents to form a silicone phase, wherein the two or more water-insoluble constituents include the at least one water-insoluble carrier and the primary emulsifier; and
    mixing the aqueous phase into the silicone phase to provide the water-in-silicone inverse phase emulsion of claim 1.

17. An analgesic composition for relieving peripheral neuropathy, the analgesic composition comprising:
    an aqueous phase comprising:
        magnesium sulfate in an amount of about 15 to about 30 weight percent of the total weight of the composition;

optional a source of vitamin B12 in an amount of about 0.001 to about 1 weight percent of the total weight of the composition;

at least one water-soluble carrier consisting of ethoxydiglycol in an amount from 0.5 to about 5 weight percent based on the total weight of the composition, glycerine and one of butylene glycol and propylene glycol;

a first additional agent from a humectant in an amount of about 1 to about 10 weight percent of the total weight of the composition;

a second additional agent from at least one preservative in an amount of about 0.5 to about 6.0 weight percent of the total weight of the composition; and water in an amount of about 35 to about 65 weight percent of the total weight of the composition; and a silicone phase comprising:

cyclomethicone in an amount of about 5 to about 25 weight percent of the total weight of the composition;

dimethicone, dimethiconol, or a mixture in an amount of about 0.7 to about 1.0 weight percent of the total weight of the composition;

a primary emulsifier in an amount of about 0.5 to about 3.0 weight percent of the total weight of the composition; and C12-15 alkyl benzoate in an amount of about 0.5 to about 5.0 weight percent of the total weight of the composition;

wherein the aqueous and silicone phases are provided as a water-in-silicone inverse phase emulsion.

* * * * *